(12) United States Patent
Tuckwell et al.

(10) Patent No.: US 8,869,794 B1
(45) Date of Patent: Oct. 28, 2014

(54) AEROSOLIZATION APPARATUS WITH CAPSULE PUNCTURING MEMBER

(75) Inventors: Jon David Tuckwell, Cambridgeshire (GB); Thomas Christopher St. Quintin, Cambridgeshire (GB)

(73) Assignee: Novartis Pharma AG, Basel (CH)

( * ) Notice: Subject to any disclaimer, the term of this patent is extended or adjusted under 35 U.S.C. 154(b) by 1617 days.

(21) Appl. No.: 10/821,652

(22) Filed: Apr. 9, 2004

Related U.S. Application Data (60) Provisional application No. 60/461,732, filed on Apr. 9, 2003.

(51) Int. Cl.
  *A61M 15/00* (2006.01)
  *B65D 83/04* (2006.01)
  *G07F 11/66* (2006.01)

(52) U.S. Cl.
  USPC .......................... 128/203.21; 206/538; 221/25

(58) Field of Classification Search
  USPC ............ 128/203.21, 205.21, 203.15; 206/538, 206/828; 221/25
  See application file for complete search history.

(56) References Cited

U.S. PATENT DOCUMENTS

| | | | |
|---|---|---|---|
| 3,012,694 A | 12/1961 | Johnston | |
| 3,809,084 A | 5/1974 | Hansen | |
| 3,837,341 A * | 9/1974 | Bell | 128/203.15 |
| 3,888,253 A * | 6/1975 | Watt et al. | 128/203.15 |
| 3,906,950 A * | 9/1975 | Cocozza | 128/203.15 |
| 3,918,451 A | 11/1975 | Steil | |
| 3,991,761 A | 11/1976 | Cocozza | |
| 4,069,819 A * | 1/1978 | Valentini et al. | 128/203.15 |
| 4,114,615 A | 9/1978 | Wetterlin | |
| 4,116,195 A | 9/1978 | James | |
| 4,247,066 A | 1/1981 | Frost et al. | |
| 4,265,236 A | 5/1981 | Pacella | |
| 4,338,931 A * | 7/1982 | Cavazza | 128/203.15 |
| 4,846,876 A | 7/1989 | Draber et al. | |
| 4,884,565 A * | 12/1989 | Cocozza | 128/203.21 |
| 4,889,114 A | 12/1989 | Kladders | |
| 4,995,385 A * | 2/1991 | Valentini et al. | 128/203.21 |
| 5,152,284 A * | 10/1992 | Valentini et al. | 128/203.21 |
| 5,201,308 A | 4/1993 | Newhouse | |

(Continued)

FOREIGN PATENT DOCUMENTS

| | | |
|---|---|---|
| EP | 0 839 544 | 5/1998 |
| EP | 1 068 874 | 1/2001 |

(Continued)

*Primary Examiner* — Patricia Bianco
*Assistant Examiner* — Tarla Patel
(74) *Attorney, Agent, or Firm* — Janah & Associates (57) ABSTRACT

An aerosolization apparatus comprises a housing defining a chamber having one or more air inlets. The chamber is sized to receive a capsule which contains an aerosolizable pharmaceutical formulation. A puncturing mechanism is provided within the housing and comprising a puncture member. The puncture member comprises a forward end shaped to form a cutting edge that is effective in cutting the wall of the capsule to create an opening into the capsule. The puncture member also comprises a trailing end shaped so that it has a non-cutting surface that does not cut the wall of the capsule when the trailing end is inserted into the opening created by the forward end. An end section is associated with the housing. The end section is sized and shaped to be received in a user's mouth or nose so that the user may inhale through the end section to inhale aerosolized pharmaceutical formulation that has exited the capsule through the opening created in the capsule.

18 Claims, 6 Drawing Sheets

(56) References Cited

U.S. PATENT DOCUMENTS

| | | | | |
|---|---|---|---|---|
| 5,263,475 A | * | 11/1993 | Altermatt et al. | 128/203.15 |
| 5,287,850 A | | 2/1994 | Haber et al. | |
| 5,301,666 A | | 4/1994 | Lerk et al. | |
| 5,379,763 A | * | 1/1995 | Martin | 128/203.15 |
| 5,458,135 A | | 10/1995 | Patton et al. | |
| 5,619,985 A | | 4/1997 | Ohki et al. | |
| 5,715,811 A | | 2/1998 | Ohki et al. | |
| 5,785,049 A | | 7/1998 | Smith et al. | |
| 5,797,391 A | * | 8/1998 | Cook et al. | 128/203.15 |
| 5,874,064 A | | 2/1999 | Edwards et al. | |
| 5,881,719 A | | 3/1999 | Gottenauer et al. | |
| 5,894,841 A | | 4/1999 | Voges | |
| 5,921,236 A | * | 7/1999 | Ohki et al. | 128/203.15 |
| 5,922,675 A | | 7/1999 | Baker et al. | |
| 5,985,309 A | | 11/1999 | Edwards et al. | |
| 5,992,675 A | | 11/1999 | Kerr | |
| 6,186,141 B1 | * | 2/2001 | Pike et al. | 128/203.12 |
| 6,230,707 B1 | | 5/2001 | Horlin | |
| 6,257,233 B1 | | 7/2001 | Burr et al. | |
| 6,357,490 B1 | | 3/2002 | Johnston et al. | |
| 6,418,926 B1 | | 7/2002 | Chawla | |
| 6,503,480 B1 | | 1/2003 | Edwards et al. | |
| 6,520,179 B1 | * | 2/2003 | Von Schuckmann et al. | 128/203.15 |
| 6,705,313 B2 | * | 3/2004 | Niccolai | 128/203.21 |
| 6,715,486 B2 | | 4/2004 | Gieschen et al. | |
| 6,732,732 B2 | * | 5/2004 | Edwards et al. | 128/203.21 |
| 6,766,799 B2 | | 7/2004 | Edwards et al. | |
| 6,892,728 B2 | | 5/2005 | Helgesson et al. | |
| 6,907,880 B1 | * | 6/2005 | Heckenmuller et al. | 128/203.15 |
| 6,948,496 B2 | * | 9/2005 | Eason et al. | 128/203.15 |
| 7,278,425 B2 | | 10/2007 | Edwards et al. | |
| 7,516,741 B2 | * | 4/2009 | Glusker et al. | 128/203.21 |
| 2003/0131847 A1 | * | 7/2003 | Niccolai | 128/203.15 |
| 2003/0150454 A1 | * | 8/2003 | Burr et al. | 128/203.21 |
| 2004/0206350 A1 | | 10/2004 | Alston et al. | |
| 2005/0000518 A1 | * | 1/2005 | Dunkley et al. | 128/203.21 |
| 2005/0022812 A1 | * | 2/2005 | Hrkach | 128/203.15 |
| 2005/0022813 A1 | * | 2/2005 | Alston | 128/203.21 |
| 2005/0051166 A1 | * | 3/2005 | Glusker et al. | 128/203.21 |
| 2005/0056280 A1 | * | 3/2005 | Alston et al. | 128/203.21 |
| 2005/0081852 A1 | * | 4/2005 | Rangachari | 128/203.21 |
| 2005/0092323 A1 | * | 5/2005 | Frietsch et al. | 128/203.15 |
| 2005/0150492 A1 | * | 7/2005 | Dunkley et al. | 128/203.21 |
| 2006/0254583 A1 | * | 11/2006 | Deboeck et al. | 128/203.15 |
| 2007/0295333 A1 | | 12/2007 | Fourment et al. | |

FOREIGN PATENT DOCUMENTS

| | | |
|---|---|---|
| WO | WO 95/24183 | 9/1995 |
| WO | WO 96/32096 | 10/1996 |
| WO | WO 96/32149 | 10/1996 |
| WO | WO 99/16419 | 4/1999 |
| WO | WO 99/16422 | 4/1999 |
| WO | WO 00/07572 | 2/2000 |
| WO | WO 00/72904 | 12/2000 |
| WO | WO 02/11802 | 2/2002 |
| WO | WO 02/083220 | 10/2002 |

* cited by examiner

FIG. 10E

AEROSOLIZATION APPARATUS WITH CAPSULE PUNCTURING MEMBER

This application claims the benefit U.S. Provisional Patent Application Ser. No. 60/461,732 filed on Apr. 9, 2003, which is incorporated herein by reference in its entirety.

BACKGROUND

The need for effective therapeutic treatment of patients has resulted in the development of a variety of techniques for delivering a pharmaceutical formulation to a patient. One traditional technique involves the oral delivery of a pharmaceutical formulation in the form of a pill, capsule, or the like. Inhalable drug delivery, where an aerosolized pharmaceutical formulation is orally or nasally inhaled by a patient to deliver the formulation to the patient's respiratory tract, has also proven to be an effective manner of delivery. In one inhalation technique, a pharmaceutical formulation is delivered deep within a patient's lungs where it may be absorbed into the blood stream. In another inhalation technique, a pharmaceutical formulation is delivered locally to a particular site, such as an infected lung. Many types of inhalation devices exist including devices that aerosolize a dry powder pharmaceutical formulation.

One type of inhalation device aerosolizes a pharmaceutical formulation that is stored in a capsule. For example, a dose or a portion of a dose of a dry powder pharmaceutical formulation may be stored in a capsule, and the capsule may be inserted into an aerosolization device which is capable of aerosolizing the pharmaceutical formulation. The aerosolization may be accomplished by releasing stored energy. For example, the aerosolization may be accomplished by utilizing energy supplied during the user's inhalation, such as the flow of inhaled air, to aerosolize the pharmaceutical formulation.

Before, during or after being inserted into the aerosolization device, the capsule is opened to expose the pharmaceutical formulation. The opening of the capsule may be performed, for example, by puncturing the capsule, tearing the capsule, or separating the parts of the capsule. When the capsule is properly opened and when aerosolization energy is supplied, the pharmaceutical formulation is aerosolized so that it may be inhaled by the user and a dose or portion of a dose of the aerosolized pharmaceutical formulation may be delivered to the user's respiratory tract.

However, improper use of the aerosolization device may result in the delivery of less than the desired amount of the pharmaceutical formulation. For example, if a capsule is not properly or completely opened before the aerosolization process, the amount of pharmaceutical formulation being aerosolized may be reduced or the flow of the aerosolized pharmaceutical formulation may not be of sufficiently high quality to deliver a desirable amount to the user. In some instances, the opening mechanism can cause damage to the capsule and/or to the aerosolization apparatus, thereby limiting the effectiveness of the pharmaceutical formulation delivery or limiting the lifetime of the apparatus.

Therefore, it is desirable to be able to improve the effectiveness and reproducibility of a capsule opening mechanism for an aerosolization apparatus. It is further desirable to be able to provide such capsule opening in a manner than increases the lifetime of the aerosolization apparatus.

SUMMARY

The present invention satisfies these needs. In one aspect of the invention, a capsule opening member has a sharpened leading end and an unsharpened trailing end to improve the effectiveness of a capsule puncture.

In another aspect of the invention, an aerosolization apparatus comprises a housing defining a chamber having one or more air inlets, the chamber being sized to receive a capsule which contains an aerosolizable pharmaceutical formulation; a puncturing mechanism within the housing and comprising a puncture member, wherein the puncture member comprises a forward end shaped to form a cutting edge that is effective in cutting the wall of the capsule to create an opening into the capsule, and wherein the puncture member comprises a trailing end shaped so that it has a non-cutting surface that does not cut the wall of the capsule when the trailing end is inserted into the opening created by the forward end; and an end section associated with the housing, the end section sized and shaped to be received in a user's mouth or nose so that the user may inhale through the end section to inhale aerosolized pharmaceutical formulation that has exited the capsule through the opening created in the capsule.

In another aspect of the invention, a method of aerosolizing a pharmaceutical formulation comprises providing a capsule containing an aerosolizable pharmaceutical formulation; advancing a puncture member through the wall of the capsule to create an opening in the capsule, wherein the puncture member comprises a forward end shaped to form a cutting edge and wherein the puncture member comprises a trailing end shaped so that it has a non-cutting surface that does not cut the wall of the capsule when the trailing end is inserted into the opening created by the forward end, wherein an opening into the capsule is created without a piece of the wall of the capsule becoming detached from the capsule; aerosolizing the pharmaceutical formulation by flowing air through the chamber; and administering the aerosolized pharmaceutical formulation to the respiratory tract of a user during the user's inhalation.

In another aspect of the invention a method of making an aerosolization apparatus comprises bending a round wire to form two ends; cutting an angled planar section from each of the two ends to form two sharpened tips; blunting the trailing section of the angled planar section to form a non-cutting trailing end; and installing the round wire with the sharpened tips into a puncturing mechanism in a aerosolization apparatus.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

DESCRIPTION

The present invention relates to an aerosolization apparatus. In particular, the invention relates to an aerosolization apparatus capable of aerosolizing a powder contained in a capsule. Although the process is illustrated in the context of aerosolizing a dry powder pharmaceutical formulation for inhalation, the present invention can be used in other processes and should not be limited to the examples provided herein.

Figure 1A:
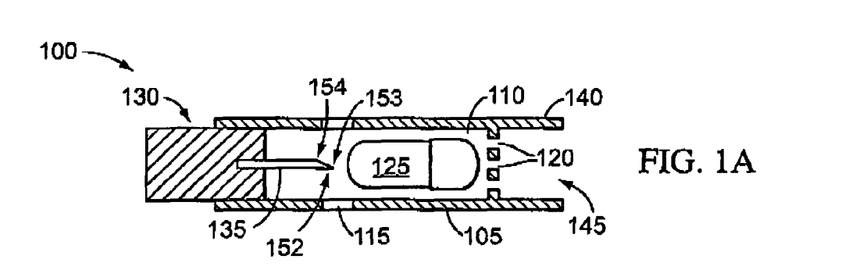
FIG. 1A is a schematic sectional side view of a version of an aerosolization apparatus in a rest position.

An aerosolization apparatus 100 according to the present invention is shown schematically in FIG. 1A. The aerosolization apparatus 100 comprises a housing 105 defining a chamber 110 having one or more air inlets 115 and one or more air outlets 120. The chamber 110 is sized to receive a capsule 125 which contains an aerosolizable pharmaceutical formulation. A puncturing mechanism 130 comprises a puncture member 135 that is moveable within the chamber 110. Near or adjacent the outlet 120 is an end section 140 that may be sized and shaped to be received in a user's mouth or nose so that the user may inhale through an opening 145 in the end section 140 that is in communication with the outlet 120.

The aerosolization apparatus 100 utilizes air flowing through the chamber 110 to aerosolize the pharmaceutical formulation in the capsule 125. For example, FIGS. 1A through 1E illustrate the operation of a version of an aerosolization apparatus 100 where air flowing through the inlet 115 is used to aerosolize the pharmaceutical formulation and the aerosolized pharmaceutical formulation flows through the outlet 120 so that it may be delivered to the user through the opening 145 in the end section 140. The aerosolization apparatus 100 is shown in its initial condition in FIG. 1A. The capsule 125 is positioned within the chamber 110 and the pharmaceutical formulation is contained within the capsule 125.

Figure 1B:
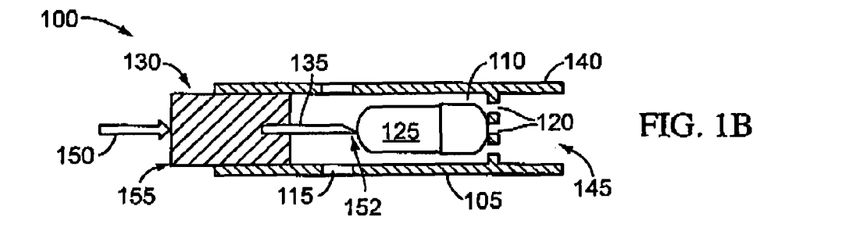
FIG. 1B is a schematic sectional side view of the version of an aerosolization apparatus shown in FIG. 1A just before capsule puncture.
Figure 1C:
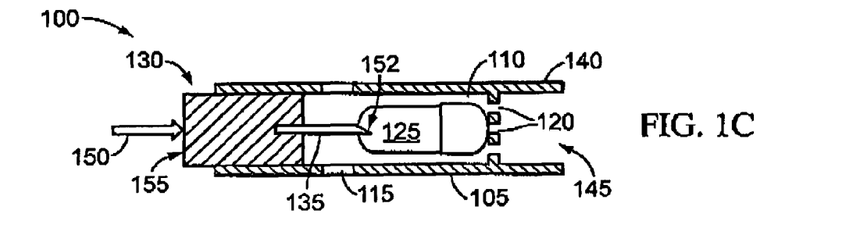
FIG. 1C is a schematic sectional side view of the version of an aerosolization apparatus shown in FIG. 1A as the capsule is being punctured.
Figure 1D:
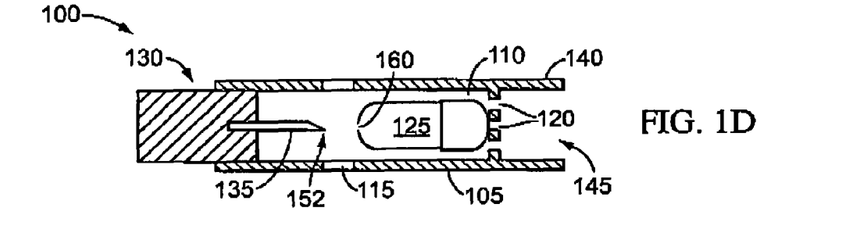
FIG. 1D is a schematic sectional side view of the version of an aerosolization apparatus shown in FIG. 1A just after capsule puncture.

To use the aerosolization apparatus 100, the pharmaceutical formulation in the capsule 125 is exposed to allow it to be aerosolized. In the version of FIGS. 1A though 1E, the puncture mechanism 130 is advanced within the chamber 110 by applying a force 150 to the puncture mechanism 130. For example, a user may press against a surface 155 of the puncturing mechanism 130 to cause the puncturing mechanism 130 to slide within the housing 105 so that the puncture member 135 contacts the capsule 125 in the chamber 110, as shown in FIG. 1B. By continuing to apply the force 150, the puncture member 135 is advanced into and through the wall of the capsule 125, as shown in FIG. 1C. The puncture member may comprise one or more sharpened tips 152 to facilitate the advancement through the wall of the capsule 125. The puncturing mechanism 130 is then retracted to the position shown in FIG. 1D, leaving an opening 160 through the wall of the capsule 125 to expose the pharmaceutical formulation in the capsule 125.

Figure 1E:
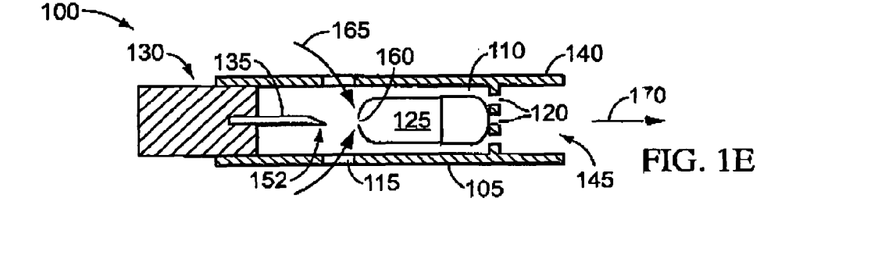
FIG. 1E is a schematic sectional side view of the version of an aerosolization apparatus shown in FIG. 1A in use.

Air or other gas then flows through an inlet 115, as shown by arrows 165 in FIG. 1E. The flow of air causes the pharmaceutical formulation to be aerosolized. When the user inhales 170 through the end section 140 the aerosolized pharmaceutical formulation is delivered to the user's respiratory tract. In one version, the air flow 165 may be caused by the user's inhalation 170. In another version, compressed air or other gas may be ejected into the inlet 115 to cause the aerosolizing air flow 165.

Proper creation of the opening 160 in the capsule 125 allows for efficient and effective delivery of the aerosolized pharmaceutical formulation to the user. In contrast, improper creation of the opening 160 can lead to inefficient and less effective delivery of the medicament to a user. Therefore a properly designed sharpened tip 152 can help in the creation of consistent openings in the capsule. Also, it is important to have a sharpened tip 152 that does not result in the portion of the wall of the capsule 125 that is removed to create the opening 160 from becoming broken off from the capsule 125 and thereby becoming one or more loose fragments. These fragments may be inhaled by the user, potentially causing discomfort.

Figure 2A:
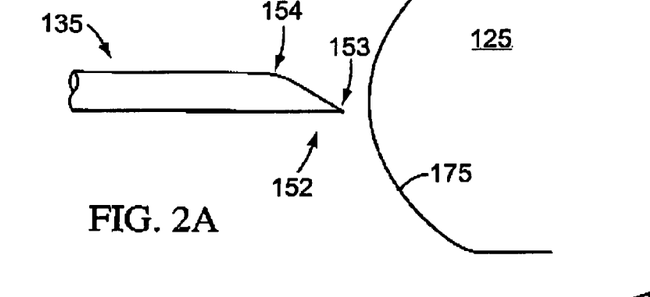
FIGS. 2A through 2D are schematic sectional side views showing the capsule puncturing process using an aerosolization apparatus as in FIG. 1A.
Figure 2B:
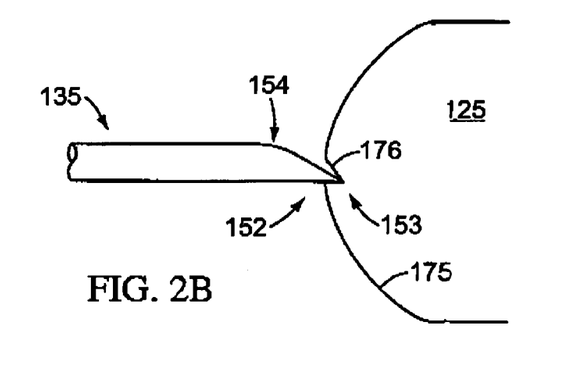
Figure 2C:
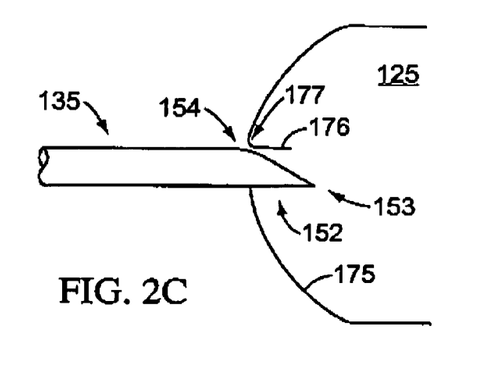
Figure 2D:
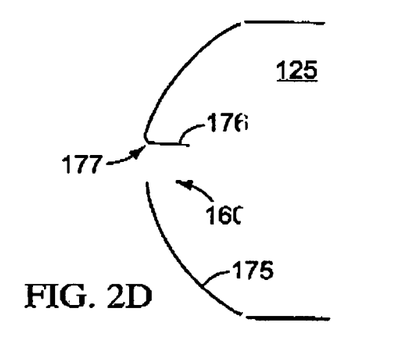

Accordingly, to increase the efficiency and effectiveness of the aerosolization apparatus 100, in one version of the present invention, the puncture member 135 comprises a sharpened tip 152 having a forward end 153 and a trailing end 154. The forward end 153 is shaped to form a cutting point or edge that is effective in cutting the wall of the capsule 125. However, the trailing end 154 is shaped so that it has a non-cutting surface. For example, in one version, the trailing end 154 may be ground so that it has a smooth profile, as shown in FIG. 2A. FIGS. 2A through 2D illustrate the capsule puncturing process using the puncture member 135 of the present invention. As the puncture member 135 is advanced from the position shown in FIG. 2A to the position shown in FIG. 2B, the cutting tip on the forward end 153 cuts the wall 175 of the capsule 170. Continued advancement of the puncturing member 135, as shown in FIG. 2C, pushes a flap 176 of wall material inward into the capsule 125. Because of the non-cutting profile of the trailing end 154, the portion 177 of the flap 176 opposite the initial cut portion is bent and plastically deformed rather than being cut, leaving an opening 160 as shown in FIG. 2D when the puncture member 135 is retracted.

The puncture member 135 having a sharpened tip 152 with a non-cutting trailing end 154 provides many advantages over prior art puncture members. For example, conventional puncture member may be formed from round wire than is sheared or ground along a plane at the trailing end or may be formed in a manner where the sharpened tip includes a non-straight edge at the trailing end, such as a curved edge formed by using a diamond shaped wire, as described in PCT application WO 02/083220 which is incorporated herein by reference in its entirety. These conventional puncture members will sometimes result in the flap 167 being cut at the portion 177 thereby causing the flap 176 to be released from the wall 175 of the capsule 180 and potentially aerosolized. However, it has been discovered that by providing a non-cutting trailing end 154, the number of loose flaps 176 is significantly reduced and more consistent punctures result. Another disadvantage that has been discovered with the conventional puncture members is that they are sometimes not adequately removed from the capsule 125. This is believed to be due to the design of the trailing end of the tips of the members which often have barbs thereon as a result of the shearing or other sharpening process. These bards will sometimes grab onto the capsule as the puncture member is being retracted and will pull the capsule rearward in the chamber 110. Even when there are no barbs, merely the shape of the trailing end of conventional puncture can cause the shaft of the puncturing member 135 to contact the sides of the opening 160 during retraction of the puncturing member 135. This contact may also lead to the capsule being pulled back into the chamber and/or may prevent the puncture member 135 from being retracted out of the capsule 125. The non-cutting trailing end 154 of the present invention, significantly reduces this problem.

Figure 3A:
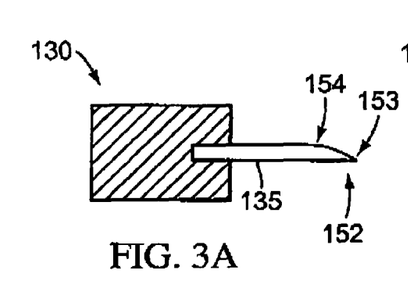
FIGS. 3A and 3B are schematic sectional side views of a version of a puncturing member.
Figure 3B:
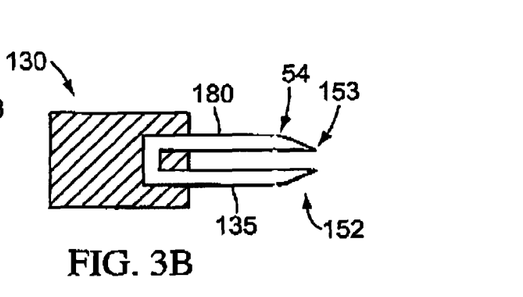
Figure 4A:
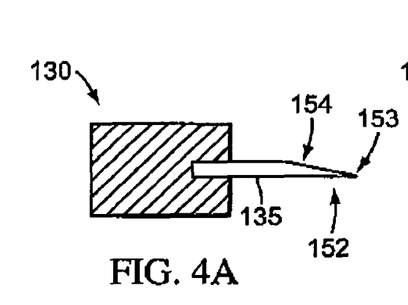
FIGS. 4A and 4B are schematic sectional side views of another version of a puncturing member.
Figure 4B:
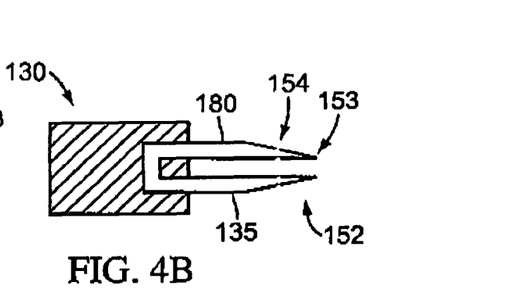
Figure 5A:
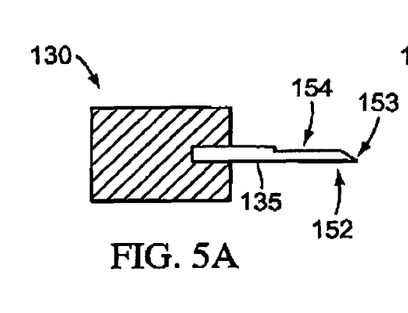
FIGS. 5A and 5B are schematic sectional side views of another version of a puncturing member.
Figure 5B:
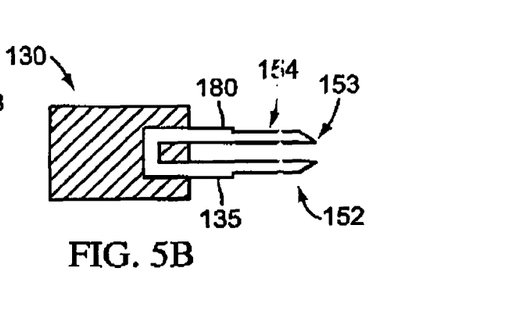
Figure 5C:
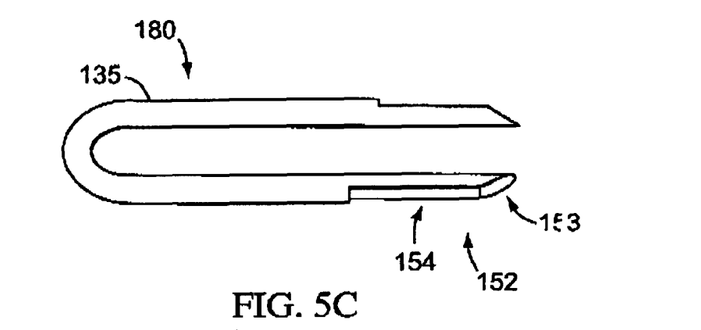
FIG. 5C is a schematic perspective view of the puncturing member shown in FIG. 5B.
Figure 6:
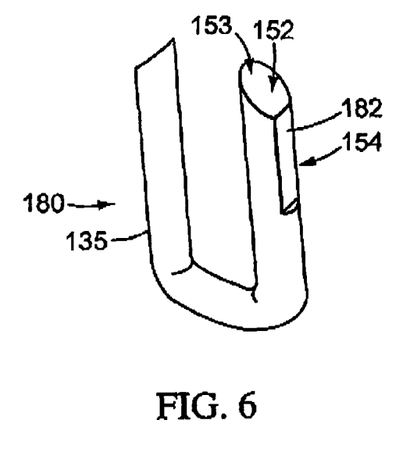
FIG. 6 is another schematic perspective view of the puncturing member shown in FIG. 5B.
Figure 7:
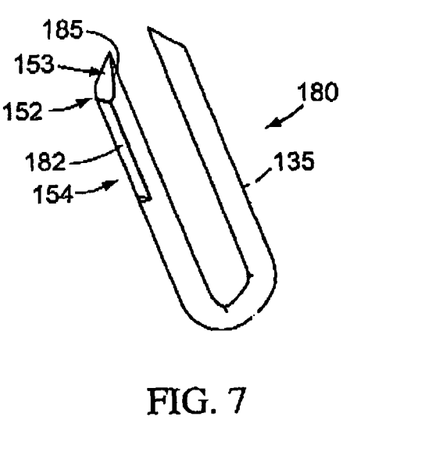
FIG. 7 is a schematic perspective view of another version of a puncturing member.
Figure 8:
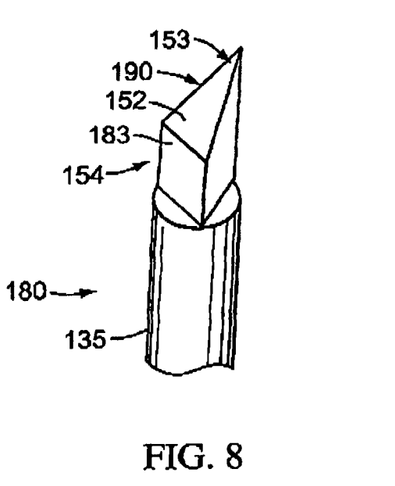
FIG. 8 is a schematic perspective view of another version of a puncturing member.
Figure 9:
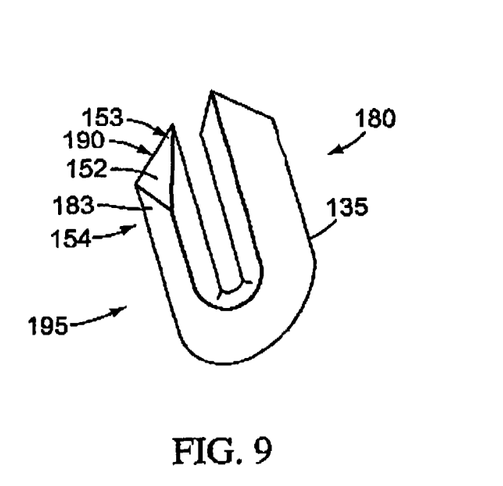
FIG. 9 is a schematic perspective view of another version of a puncturing member.

The non-cutting trailing end 154 of the sharpened tip 152 may be provided by grinding the trailing end 154, as discussed above, or by otherwise shaping the sharpened tip 152. Examples of sharpened tips 152 having non-cutting trailing ends are shown in FIGS. 3A, 3B, 4A, 4B, 5A, 5B, 5C, and 6-9. The version of FIG. 3A is much like the version of FIGS. 2A though 2D where the trailing end 154 is ground to a smooth profile. The version of FIG. 3B is similar to that of FIG. 3A, but with two sharpened tips 152 being provided to create two openings in a capsule. Alternatively, three or more sharpened tips may be provided to create three or more openings in a capsule. In the version of FIG. 3B, the two tips are provided on the opposite ends of a U-shaped puncture member 180. Alternatively, other shapes may be used, such as two straight and separate pins. In the versions of FIGS. 4A and 4B, the sharpened tip 152 is provided by making a planar cut or grind in the puncture member 135. In this version, the cut is of sufficient length that the trailing end of the cut never contacts the capsule 125. Thus, the trailing end remains outside of the capsule. Accordingly, the trailing end 154 does not contact the capsule. Instead, capsule contact is limited to an intermediate portion of the cut, preferably at the midpoint, as shown in FIG. 4A and the capsule is not subjected to the deleterious effects of the more rearward portion. In one version of the aerosolization apparatus, the advancement of the puncture member of FIGS. 4A and 4B is limited to prevent the exposure of the capsule to a cutting trailing end. In the version of FIGS. 5A, 5B, and 5C, a conventional round wire with a planar cut tip is further processes to cut away the trailing end 154 thereby removing the cutting portion of the trailing end. This provides a substantially D-shaped sharpened tip 152 as shown in FIG. 5C. FIG. 6 shows another view of the sharpened tip 152 of FIG. 5C. The straight edge 182 is advantageous over a rounded or pointed edge of a conventional puncture member in reducing the number of loose flaps 176, in reducing the likelihood of the puncture member being captured within the capsule, and in reducing wear and tear on the aerosolization apparatus 100 in that the conventional edges often produce plastic shaving from contacted surfaces in the apparatus. The version of FIG. 7 is similar to the version of FIG. 6 but with one or more facets 185 being provided at the leading end 153 in order to facilitate advancement of the tip through the capsule wall 175. In the version of FIGS. 8 and 9, the sharpened tip 152 is formed into a substantially triangular shape 190. The straight edge 183 that results from the triangular shape 190 is advantageous is much the same manner as the edge 182 that results from the D-shape tip. The sharpened tip 152 of the version of FIG. 8 is formed by cutting away the sides to form the triangular shape 190. In the version of FIG. 9, a triangular wire 195 is bent and then shaped to form the triangular shaped 190 sharpened tip 152.

It has been found to be advantageous to form the puncture member 135 out of a round, preferably circular, wire that is substantially free of planar surfaces prior to the formation of the sharpened tip 152. For example, the sharpened edge formed by cutting the round wire is advantageous over sharpened points formed by cutting wire having planar surfaces because the round edge more evenly and consistently penetrates the capsule wall without the abrupt penetration changes that can occur with planar wires. These abrupt changes can lead to inconsistent fracturing of the wall of the capsule and an increased risk of the portion of the capsule wall becoming separated from the capsule. In addition, the round wire is widely available and is more easily shapeable. For example, it is more difficult to bend a wire having a corner about the corner than it is to bend a round wire.

A version of an aerosolization apparatus 100 comprising a puncture member 135 having a sharpened tip 152 with a cutting leading end 153 and a non-cutting trailing end 154 is shown in FIGS. 10A through 10E. In this version, the housing 105 of the aerosolization apparatus 100 comprises a body 205 and a removable endpiece 210. The endpiece 210 may be removed from the body 205 to insert a capsule 125 in the chamber 110 which is formed when the body 205 and the endpiece 210 are connected together. The endpiece 210 comprises a partition 215 that blocks the forward end of the chamber 110, and the partition 215 has the one or more outlets 120 extending therethrough. An example of an aerosolization apparatus with a partition 215 and chamber 110 is described in U.S. Pat. No. 4,069,819 and in U.S. Pat. No. 4,995,385, both of which are incorporated herein by reference in their entireties. In such an arrangement, the chamber 110 comprises a longitudinal axis that lies generally in the inhalation direction, and the capsule 125 is insertable lengthwise into the chamber 110 so that the capsule's longitudinal axis may be parallel to the longitudinal axis of the chamber 110. In the version of FIGS. 10A through 10E, the chamber 110 is sized to receive a capsule 125 containing a pharmaceutical formulation in a manner which allows the capsule to move within the chamber 110. The inlets 115 comprise a plurality of tangentially oriented slots 220. When a user inhales 170 through the endpiece 210, outside air is caused to flow through the tangential slots 220 as shown by arrows 225 in FIG. 10E. This airflow 225 creates a swirling airflow within the chamber 110. The swirling airflow causes the capsule 125 to contact the partition 215 and then to move within the chamber 110 in a manner that causes the pharmaceutical formulation to exit the capsule 125 and become entrained within the swirling airflow. In one version, the capsule 125 may rotate within the chamber 110 in a manner where the longitudinal axis of the capsule is remains at an angle less than 80 degrees, and preferably less than 45 degrees from the longitudinal axis of the chamber. The movement of the capsule 125 in the chamber 110 may be caused by the width of the chamber 110 being less than the length of the capsule 125. In one specific version, the chamber 110 comprises a tapered section 230 that terminates at an edge 235. During the flow of swirling air in the chamber 110, the forward end of the capsule 125 contacts and rests on the partition 215 and a sidewall of the capsule 125 contacts the edge 235 and slides and/or rotates along the edge 235. This motion of the capsule is particularly effective in forcing a large amount of the pharmaceutical formulation through one or more openings 160 in the rear of the capsule 125.

Figure 10A:
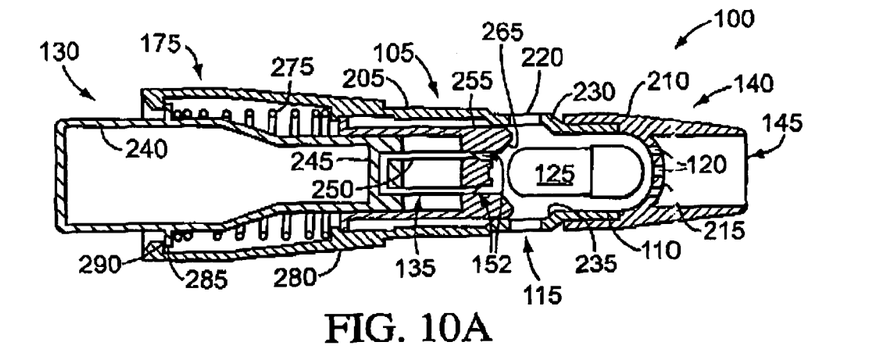
FIG. 10A is a schematic sectional side view of another version of an aerosolization apparatus in a rest position.
Figure 10B:
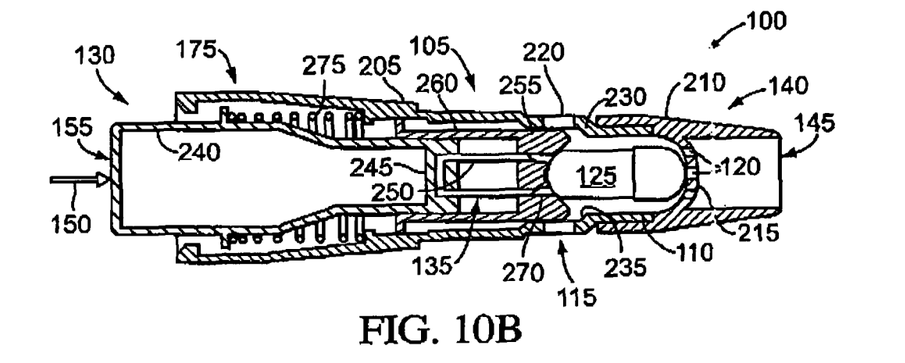
FIG. 10B is a schematic sectional side view of the version of an aerosolization apparatus shown in FIG. 10A just before capsule puncture.
Figure 10C:
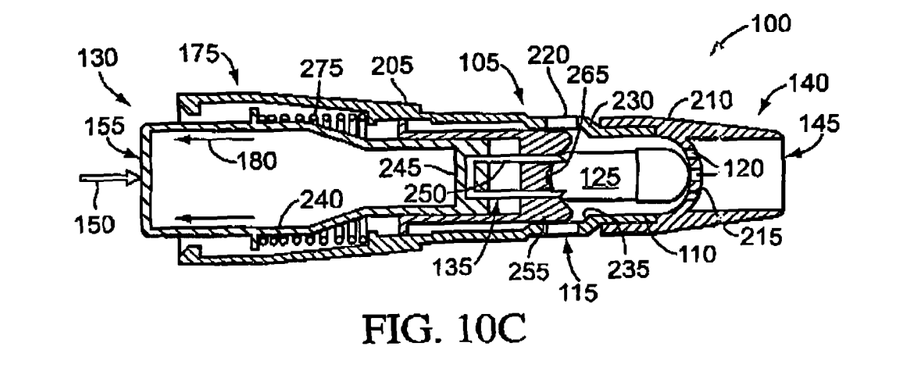
FIG. 10C is a schematic sectional side view of the version of an aerosolization apparatus shown in FIG. 10A as the capsule is being punctured.
Figure 10D:
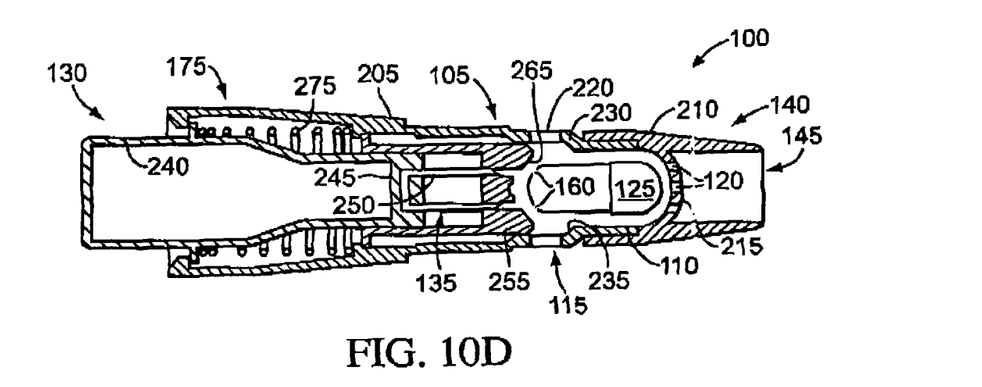
FIG. 10D is a schematic sectional side view of the version of an aerosolization apparatus shown in FIG. 10A just after capsule puncture.
Figure 10E:
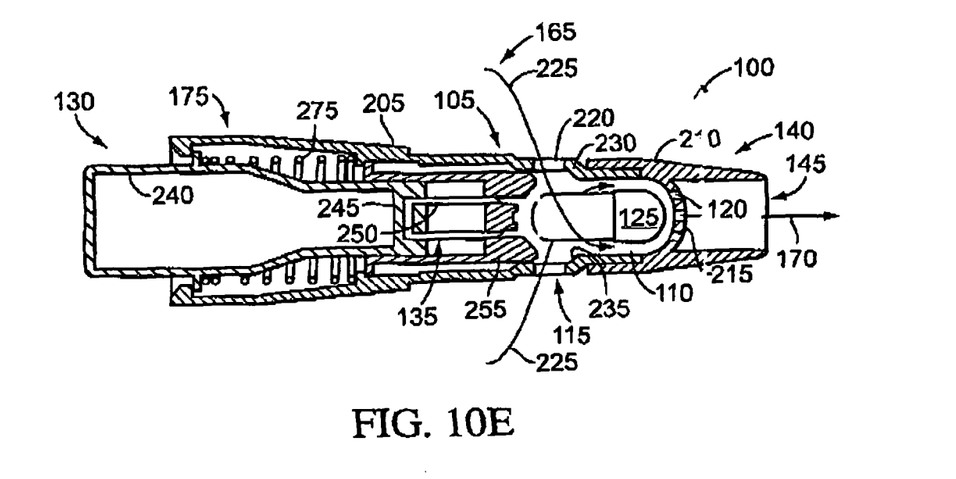
FIG. 10E is a schematic sectional side view of the version of an aerosolization apparatus shown in FIG. 10A in use.

The one or more openings 160 in the rear of the capsule 125 in the version of FIGS. 10A through 10E are created by a puncturing mechanism 130 having a puncture member 135 such as any of those described above that is slidable within the body 205. The puncturing mechanism 130, shown in its rest position in FIG. 10A, comprises a plunger 240 attached at its forward end 245 to the puncture member 135, which in the version shown is a U-shaped staple 250 having two sharpened tips 152 as in any version described above or the like. The puncturing mechanism 130 further comprises a alignment member 255 which contacts the plunger 240 and/or the puncture member 135 and is slidable relative to the plunger 240 and the puncture member 135. To create the openings 160 in the capsule 125, the user applies a force 150 to the plunger 240, as shown in FIG. 10B, such as by pressing against the end surface 155 of the plunger 240 with the user's finger or thumb. The force 150 causes the plunger to slide within the body 205. A slight frictional contact between the plunger 240 the a rear section 260 of the alignment member 255 causes the alignment member 255 to also slide within the body 205 until a forward seating surface 265 of the alignment member 255 contacts the capsule 125, as shown in FIG. 10B. The forward seating surface 265, which may be shaped to generally match the shape of the capsule 125, secures the capsule 125 between the alignment member 255 and the partition 215. The continued application of force 150 causes the plunger 240 and the puncture member 135 to slide relative to the alignment member 255, as shown in FIG. 10C, to advance the puncture member 135 through openings 270 in the forward seating surface 265 and into the capsule 125. Upon the removal of the force 150, a spring 275 or other biasing member urges the puncturing mechanism 130 back to its rest position. For example, the spring 275 may contact a shoulder 280 in the body 205 and press a flange 285 on the plunger 240 toward a rim 290 in the body 205. The frictional engagement between the plunger 240 and the alignment member 255 also returns the alignment member 255 to its retracted position when the plunger is returned to its retracted position.

In another version, the aerosolization apparatus 100 may be configured differently than as shown in FIGS. 1A through 1D and 10A through 10E. For example, the chamber 100 may be sized and shaped to receive the capsule 125 so that the capsule 125 is orthogonal to the inhalation direction, as described in U.S. Pat. No. 3,991,761. As also described in U.S. Pat. No. 3,991,761, the puncturing mechanism 130 may puncture both ends of the capsule 125. In such version, the puncture member 135 of the present invention may be provided to puncture one or both ends of the capsule 125. In another version, the chamber may receive the capsule 125 in a manner where air flows through the capsule 125 as described for example in U.S. Pat. No. 4,338,931 and in U.S. Pat. No. 5,619,985. In another version, the aerosolization of the pharmaceutical formulation may be accomplished by pressurized gas flowing through the inlets, as described for example in U.S. Pat. No. 5,458,135, U.S. Pat. No. 5,785,049, and U.S. Pat. No. 6,257,233, or propellant, as described in PCT Publication WO 00/72904 and U.S. Pat. No. 4,114,615. All of the above references being incorporated herein by reference in their entireties.

In a preferred version, the invention provides a system and method for aerosolizing a pharmaceutical formulation and delivering the pharmaceutical formulation to the respiratory tract of the user, and in particular to the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperature (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), both of which are incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a dry powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 μm MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

In one version, as discussed above, the pharmaceutical formulation may be contained within a capsule 125. The capsule 125 may be of a suitable shape, size, and material to contain the pharmaceutical formulation and to provide the pharmaceutical formulation in a usable condition. For example, the capsule may comprise a wall which comprises a material that does not adversely react with the pharmaceutical formulation. In addition, the wall may comprise a material that allows the capsule to be opened to allow the pharmaceutical formulation to be aerosolized. In one version, the wall comprises one or more of gelatin, hydroxypropyl methylcellulose (HPMC), polyethyleneglycol-compounded HPMC, hydroxyproplycellulose, agar, or the like. In one version, the capsule may comprise telescopically adjoining sections, as described for example in U.S. Pat. No. 4,247,066 which is incorporated herein by reference in its entirety. The size of the capsule may be selected to adequately contain the dose of the pharmaceutical formulation. The sizes generally range from size 5 to size 000 with the outer diameters ranging from about 4.91 mm to 9.97 mm, the heights ranging from about 11.10 mm to about 26.14 mm, and the volumes ranging from about 0.13 ml to about 1.37 ml, respectively. Suitable capsules are available commercially from, for example, Shionogi Qualicaps Co. in Nara, Japan and Capsugel in Greenwood, S.C. After filling, a top portion may be placed over the bottom portion to form the a capsule shape and to contain the powder within the capsule, as described in U.S. Pat. No. 4,846,876, U.S. Pat. No. 6,357,490, and in the PCT application WO 00/07572 published on Feb. 17, 2000, all of which are incorporated herein by reference in their entireties.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the cooperating components may be reversed or provided in additional or fewer number. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. An aerosolization apparatus comprising:
a housing defining a chamber having one or more air inlets, the chamber being sized to receive a capsule which contains an aerosolizable pharmaceutical formulation;
a puncturing mechanism within the housing and comprising a puncture member that may be urged into said capsule, wherein the puncture member comprises a round wire comprising a tip comprising a forward end shaped to form a cutting edge that is effective in cutting the wall of the capsule to create an opening into the capsule, the tip further comprising a trailing end which comprises an angled planar portion that is insertable into the opening created by the cutting edge and having a length sufficient that the rearward end of the angled planar portion of the trailing end remains outside of the capsule, and thereby does not cut a wall thereof when the puncture member is urged fully into said capsule; and an end section associated with the housing, the end section sized and shaped to be received in a user's mouth or nose so that the user may inhale through the end section to inhale aerosolized pharmaceutical formulation that has exited the capsule through the opening created in the capsule.

2. An aerosolization apparatus according to claim 1 wherein the end section is removably connected to the housing and wherein the end section may be removed from the housing to provide access to the chamber.

3. An aerosolization apparatus according to claim 1 wherein the puncture mechanism comprises a pair of puncture members.

4. An aerosolization apparatus according to claim 1 wherein the puncture member is adapted to puncture only one end of the capsule.

5. An aerosolization apparatus according to claim 1 wherein the chamber is elongated and has a longitudinal axis, and wherein the longitudinal axis of the chamber and the longitudinal axis of the capsule form an angle of less than about 45 degrees during use.

6. An aerosolization apparatus according to claim 1 wherein the chamber is elongated and wherein the capsule is received lengthwise within the elongated chamber.

7. An aerosolization apparatus according to claim 1 wherein the width of the chamber is less than the length of the capsule.

8. An aerosolization apparatus according to claim 1 wherein the inlet is shaped to create a swirling airflow within the chamber.

9. An aerosolization apparatus comprising:
a housing defining a chamber having one or more air inlets, the chamber being sized to receive a capsule which contains an aerosolizable pharmaceutical formulation;
a puncturing mechanism within the housing and comprising a puncture member, wherein the puncture member comprises a round wire comprising a curved forward end shaped to form a cutting edge that is effective in cutting the wall of the capsule to create an opening into the capsule, and wherein the puncture member comprises a trailing end shaped so that it has a non-cutting surface that does not cut the wall of the capsule when the trailing end is inserted into the opening created by the forward end, the puncture member trailing end comprising a straight edge generally parallel to a tangent at a midpoint of the curved forward end, the puncture member further comprising an angled planar surface intermediate to said curved forward end and to said straight surface, wherein the angled planar surface is insertable into the opening created in the capsule; and
an end section associated with the housing, the end section sized and shaped to be received in a user's mouth or nose so that the user may inhale through the end section to inhale aerosolized pharmaceutical formulation that has exited the capsule through the opening created in the capsule.

10. An aerosolization apparatus according to claim 9 wherein the forward end comprises a terminus of said planar portion of the round wire.

11. An aerosolization apparatus comprising:
a housing defining a chamber having one or more air inlets, the chamber being sized to receive a capsule which contains an aerosolizable pharmaceutical formulation;
a puncturing mechanism within the housing and comprising a puncture member, wherein the puncture member comprises a round wire comprising a forward end shaped to form a cutting edge that is effective in cutting the wall of the capsule to create an opening into the capsule and wherein the puncture member forward end is not pointed, and wherein the puncture comprises a trailing end shaped so that it has a non-cutting surface that does not cut the wall of the capsule when the trailing end is inserted into the opening created by the forward end wherein the puncture member trailing end comprises a straight edge opposite to the forward end cutting edge, and intermediate to the straight edge and the forward end cutting edge is a planar portion that is insertable into the opening created in the capsule; and
an end section associated with the housing, the end section sized and shaped to be received in a user's mouth or nose so that the user may inhale through the end section to inhale aerosolized pharmaceutical formulation that has exited the capsule through the opening created in the capsule.

12. An aerosolization apparatus comprising:
a housing defining a chamber having one or more air inlets, the chamber being sized to receive a capsule which contains an aerosolizable pharmaceutical formulation;
a puncturing mechanism within the housing and comprising a puncture member that may be urged into, and contact, said capsule, wherein the puncture member has a tip, which comprises a curved forward end shaped to form a cutting edge that is effective in cutting the wall of the capsule to create an opening into the capsule, the tip further comprising a trailing end shaped so that it has a non-cutting surface that does not cut the wall of the capsule when the trailing end is inserted into the opening created by the forward end, and wherein the puncture member comprises a round wire having a circular cross-section and wherein the forward end and said trailing end are formed by a planar, angular cut portion of the round wire and said trailing end further comprises a flat, planar surface generally parallel to a tangent at a midpoint of the curved forward end, wherein said tip has a generally D-shaped cross section; and
an end section associated with the housing, the end section sized and shaped to be received in a user's mouth or nose so that the user may inhale through the end section to inhale aerosolized pharmaceutical formulation that has exited the capsule through the opening created in the capsule.

13. An aerosolization apparatus comprising:
a housing defining a chamber having one or more air inlets, the chamber being sized to receive a capsule which contains an aerosolizable pharmaceutical formulation;
a puncturing mechanism within the housing and comprising a generally U-shaped puncture member having a generally circular cross-section, the puncture member having a tip for urging into a capsule, wherein the tip comprises a forward end shaped to form a cutting edge that is effective in cutting the wall of the capsule to create an opening into the capsule, the tip further comprising a trailing end comprising a straight edge generally perpendicular to an axis bisecting said non-pointed forward end, the tip further comprising an angled planar surface intermediate to the non-pointed forward end and to the straight edge and wherein the tip comprises a D-shaped surface; and an end section associated with the housing, the end section sized and shaped to be received in a user's mouth or nose so that the user may inhale through the end section to inhale aerosolized pharmaceutical formulation that has exited the capsule through the opening created in the capsule.

14. A method of aerosolizing a pharmaceutical formulation, the method comprising:

providing a capsule containing an aerosolizable pharmaceutical formulation;

advancing a puncture member through the wall of the capsule to create an opening in the capsule, wherein the puncture member comprises a round wire comprising a tip having a forward end shaped to form a cutting edge and a trailing end wherein said tip comprises an angled planar portion intermediate to said forward end and to said trailing end, the planar portion having a length sufficient that the trailing end remains outside of the capsule when the tip and the angled planar portion is urged fully into said capsule, and wherein an opening into the capsule is created;

aerosolizing the pharmaceutical formulation by flowing air through the chamber; and administering the aerosolized pharmaceutical formulation to the respiratory tract of a user during the user's inhalation.

15. A method according to claim 14 wherein the puncture member comprises a round wire and wherein the forward end is a planar portion of the round wire.

16. A method of aerosolizing a pharmaceutical formulation, the method comprising:

providing a capsule containing an aerosolizable pharmaceutical formulation;

advancing a puncture member through the wall of the capsule to create an opening in the capsule, wherein the puncture member comprises a round wire comprising a curved forward end shaped to form a cutting edge, and wherein the puncture member comprises a trailing end shaped to have a straight edge so that it has a non-cutting surface that does not cut the wall of the capsule when the trailing end is inserted into the opening created by the forward end wherein said straight edge is generally parallel to a tangent at a midpoint of the curved forward end, wherein an opening into the capsule is created;

aerosolizing the pharmaceutical formulation by flowing air through the chamber; and administering the aerosolized pharmaceutical formulation to the respiratory tract of a user during the user's inhalation.

17. A method of aerosolizing a pharmaceutical formulation, the method comprising:

providing a capsule containing an aerosolizable pharmaceutical formulation;

advancing a puncture member through the wall of the capsule to create an opening in the capsule, wherein the puncture member comprises a tip having a generally circular cross-section and a curved forward end shaped to form a cutting edge and a trailing end comprising a straight edge generally perpendicular to an axis bisecting the curved forward end, and shaped to have a non-cutting surface that does not cut the wall of the capsule when the trailing end is inserted into the opening created by the curved forward end, said forward end and said trailing end formed by an angled planar portion of the tip, wherein the tip comprises a D-shaped surface, and wherein an opening into the capsule is created;

aerosolizing the pharmaceutical formulation by flowing air through the chamber; and administering the aerosolized pharmaceutical formulation to the respiratory tract of a user during the user's inhalation.

18. A puncture member for puncturing a puncturable container, the puncture member comprising a generally round wire material having a tip, the tip comprising an angled planar surface comprising a curved forward end to form a cutting edge that is effective in cutting the wall of a puncturable container to create an opening into the puncturable container, the tip further comprising a trailing end dimensioned and shaped to have a straight edge comprising a non-cutting surface wherein said straight edge does not cut the wall of the puncturable container when the trailing end is inserted into the opening created by the forward end, and wherein the trailing end further comprises a flat surface generally parallel to a tangent at a midpoint of the curved forward end and wherein said tip has a generally D-shaped cross-section.

* * * * *